United States Patent [19]

Blass

[11] 4,287,028
[45] Sep. 1, 1981

[54] ELECTROCHEMICAL DETECTION PROCEDURE FOR THE DETERMINATION OF GLUCOSE IN BIOLOGICAL FLUIDS

[76] Inventor: Karl G. Blass, 148 Cardinal Crescent, Regina, Saskatchewan, Canada

[21] Appl. No.: 157,207

[22] Filed: Jun. 6, 1980

[30] Foreign Application Priority Data

Jun. 13, 1979 [GB] United Kingdom ............ 20637/79

[51] Int. Cl.³ ............................................. G01N 27/52
[52] U.S. Cl. ................................ 204/1 T; 23/230 B; 23/901
[58] Field of Search .......... 204/1 T, 1 N, 1 K, 195 B, 204/195 R; 422/98; 23/901, 230 B; 128/635

[56] References Cited

U.S. PATENT DOCUMENTS

| | | | |
|---|---|---|---|
| 3,869,348 | 3/1975 | Gindler | 195/99 |
| 3,953,297 | 4/1976 | Gindler | 195/103.5 R |
| 4,105,522 | 8/1978 | Friedenberg et al. | 204/195 B |
| 4,127,448 | 11/1978 | Schick et al. | 204/1 T |

OTHER PUBLICATIONS

James B. Sumner, J. Biol. Chem., 62, 287–290, (1924).
James B. Sumner, J. Biol. Chem., 47, 5–7, (1921).
Rachel S. Leech et al., J. Lab. & Clin. Med., 33, 644–650, (1948).
James B. Sumner et al., Arch. Biochem., 4, 333–336, (1944).
James J. Short, J. Lab. & Clin. Chem., 18, 641–643, (1933).
James B. Sumner, J. Biol. Chem., 65, 393–395, (1925).
Chemical Abstracts, 5346c (1960).
D. J. Bell et al., J. Chem. Soc. London, 3760–3763, (1952).
F. Hostettler et al., Helv. Chim. Acta., 34, 2132–2139, (1951).
Rolf Brodersen et al., J. Lab. Clin., Med., 34, 1447–1456, (1949).
Elias Amador, Am. J. Clin. Path., 59, 735–740, (1973).
Ronald L. Searcy et al., Am. J. Clin. Path., 46, 582–586, (1966).
Benjamin Fingerhut et al., Clin. Chem. 11, 862–868, (1965).
Richard J. Henry et al., Clin. Chem., 5, 434–452, (1960).
S. K. Meur et al., Z. Anal. Chem., 283, 195–197, (1977).
M. Van Bezeij et al., Pharmaceutisch Weekblad, 111, 505–510, (1976),
Dieter Scholze, Die Lebensmittel-Ind., 21, 255–259, (1974).
Robert Bittman, J. Chem. Education, 51, 46–47, (1974).

Primary Examiner—G. L. Kaplan
Attorney, Agent, or Firm—Stanley G. Ade

[57] ABSTRACT

A method is disclosed for determining glucose whereby glucose is reacted with an aromatic reagent containing one or more nitro groups and the reaction is monitored at electrodes which measure the current produced by the reduction of one or more of the nitro groups.

1 Claim, 8 Drawing Figures

ELECTROCHEMICAL DETECTION PROCEDURE FOR THE DETERMINATION OF GLUCOSE IN BIOLOGICAL FLUIDS

BACKGROUND OF THE INVENTION

This invention relates to new and useful improvements in electrochemical detection procedures for the determination of glucose in biological fluids.

The determination of glucose in biological fluids is probably the most requested laboratory test. Glucose measurements are commonly performed on whole blood, serum, urine and cerebrospinal fluid samples.

Carbohydrate production is affected in numerous physiological and pathological conditions. For example, elevations of blood glucose have been observed in pancreatic disease, severe thyrotoxicosis, diabetes Mellitus, Phaeochromocytoma, pituitary and adrenal disorders, etc. Similarly, decreases of blood glucose have been observed in pancreatic islet cell hyperplasia, insulin overdosage, adrenal cortical insufficiency, hypopituitarism, acute infections, liver disease, poisonings and the like.

Colorimetric procedures employing 3,5-dinitrosalicylic acid (3,5-DNSA) for the determination of glucose and other reducing substances are well documented throughout the chemical literature (see Refs. 1-20). Furthermore, specificity for glucose is claimed (Refs. 4,7,14) and attributed to the physiologic context in which the method is employed (Ref. 7). Modified colorimetric procedures have been developed for the analysis of reducing sugars in blood (Refs. 4, 15,16), urine (Refs. 7,14,16-19) and for a variety of nutrients (Refs. 5,6,11) e.g. beet pulp, oatmeal cereal, milk, strawberries, vegetables and the like. Automated procedures are described for routine blood (Ref. 4) and urine (Ref. 7) sugar analyses. Recently, saccharogenic detection systems have been adapted to determine serum (Refs. 2,8-10), and urine (Ref. 10) amylase. These saccharogenic amylase methods are reported to be superior to conventional iodometric procedures (Ref. 8).

SUMMARY OF THE INVENTION

The process described herein may be employed to determine the concentration of glucose in serum samples. Modified procedures employing the same principle may similarly be developed to measure glucose in other fluids or solids brought into solution. The process, with or without modification, may be adapted to polarographic and other electrochemical apparatus currently available, or specific analyzers may more economically be built to monitor the decrease of the functional nitro group or groups contained in the reagent employed e.g. 2,4-DNP, 3,5-DNSA, 3,5-DNBA, or other aromatic nitro containing compound.

The quantitative detection procedure described herein for the electrochemical determination of glucose and other reducing substances is nitro reaction group specific and more sensitive than previously reported colorimetric procedures. Chromogenic and turbidimetric interferences are eliminated due to the nature of the detection system.

In accordance with the invention there is provided a process for the electrochemical determination of the concentration of glucose in a sample of serum, other fluid or solid brought into solution; whereby, the sample is reacted at elevated temperatures in an alkaline medium containing an aromatic reagent with one or more attached nitro groups. The resulting chemical changes, which the reactive nitro group or groups have undergone, are monitored by electrodes in terms of current changes and the glucose concentration of the sample is established by conventional techniques such as calibration curves, standard addition process, and the like.

In the analyses included herein by way of examples, the following chemicals were obtained from Fisher Scientific Co., Fair Lawn, N.J.: Fisher Certified anhydrous D-glucose, sodium hydroxide, sodium chloride, 3,5-dinitrobenzoic acid (3,5-DNBA) and reagent grade 2,4-dinitrophenol (2,4-DNP). Reagent grade 3,5-dinitrosalicylic acid was purchased from the Eastman Kodak Co., Rochester, N.Y. Triple distilled mercury was obtained from Engelhard Industries of Canada, Ltd., Toronto, Ontario. Certified quality nitrogen was supplied by Canadian Liquid Air, Ltd. However other sources of chemicals can of course be used.

All analyses were performed in a 10-ml Heyrovsky polarographic cell. A dropping mercury electrode (DME) was the indicator electrode and a mercury pool served as the reference electrode. The characteristics of the capillary used were: $m=0.596$ mg s$^{-1}$, $t=1s$, $m^{2/3}t^{1/6}=0.708$ mg$^{2/3}$s$^{\frac{1}{2}}$ for a drop time setting of 1 second, and $m=0.566$ mg s$^{-1}$, $t=2$ s, $m^{2/3}t^{1/6}=0.767$ mg$^{2/3}$s$^{\frac{1}{2}}$ for a drop-time setting of 2 seconds. Polarographic analysis was performed with a Model 170 Electrochemistry System from the Princeton Applied Research Corporation, Princeton, N.J., U.S.A.

The above data are for reference purposes only.

With the foregoing in view, and other advantages as will become apparent to those skilled in the art to which this invention relates as this specification proceeds, the invention is herein described by reference to the accompanying drawings forming a part hereof, which includes a description of a typical embodiment of the principles of the present invention, in which:

DESCRIPTION OF THE DRAWINGS

In the drawings like characters of reference indicate corresponding parts in the different figures.

DETAILED DESCRIPTION

Proceeding therefore to describe the invention in detail, the following methods were used in preparing the necessary standards:

Reaction of Glucose with 2,4-Dinitrophenol

Figure 1:
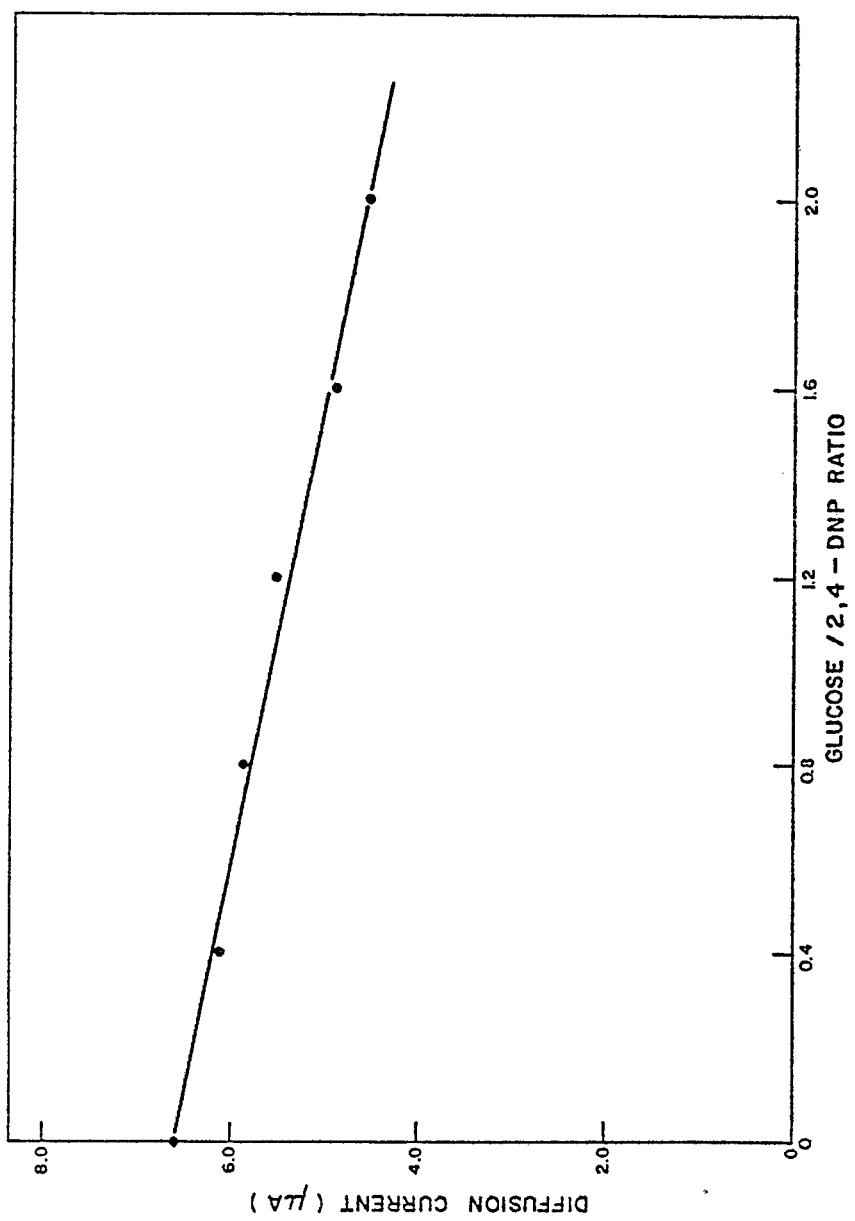
FIG. 1 is a plot showing the diffusion current results of the reaction of glucose with 2,4-Dinitrophenol plotted versus the glucose: 2,4-DNP ratio.

Fourteen milligrams of 2,4-dinitrophenol and 25 milliliters of 1.0 N NaOH were added to a 50-ml volumetric flask which was brought to volume with distilled water. This produced a $1.5 \times 10^{-3}$ M 2,4-DNP stock standard. A $7.5 \times 10^{-2}$ M glucose solution was prepared by adding 1.3512 g of glucose to a 100-ml volumetric flask which was brought to volume with distilled water. Twenty microliters of the glucose solution and 2.5 milliliters of the 2,4-dinitrophenol stock were pipetted into a 10-ml volumetric flask using a Gilford automatic pipetter/diluter. This resulted in a glucose: 2,4-DNP molar ratio of 0.4. The solution was mixed, heated in a boiling water bath for 5 minutes, cooled, and brought to volume with distilled water. Five milliliters were transferred into a 10-ml volumetric flask. Two and a half milliliters of 1.0 N NaOH were added and the flask was mixed and brought to volume with distilled water. This working standard was transferred into a 10-ml Heyrovsky cell which contained a small pool of mercury on the floor of the cell to act as the anodic reference electrode. The Heyrovsky cell was placed under a dropping mercury electrode onto which a drop timer was attached. The mercury reservoir was raised to a height of 59.0 cm. Polarograms were recorded throughout the voltage range of $-0.3$ to $-1.75$ volts. A series of working standards was similarly prepared by increasing the glucose concentration to produce molar ratios between 0.4:1 and 2:1 in increments of 0.4. All working standards and appropriate reagent blanks were tested as described above. The total diffusion current for the first and second nitro group reduction waves was determined by measuring the vertical distance from the residual current to the limiting current. The diffusion current results were plotted versus the glucose: 2,4-DNP ratio (Table I and FIG. 1).

TABLE I

Effect of Glucose Concentration on the Total Diffusion Current of the 2,4-DNP Reduction Waves

| Glucose/2,4-DNP Ratio | Total Diffusion Current ($\mu$A) |
| --- | --- |
| 0 | 6.57 |
| 0.4 | 6.14 |
| 0.8 | 5.87 |
| 1.2 | 5.54 |
| 1.6 | 4.92 |
| 2.0 | 4.57 |

Figure 2:
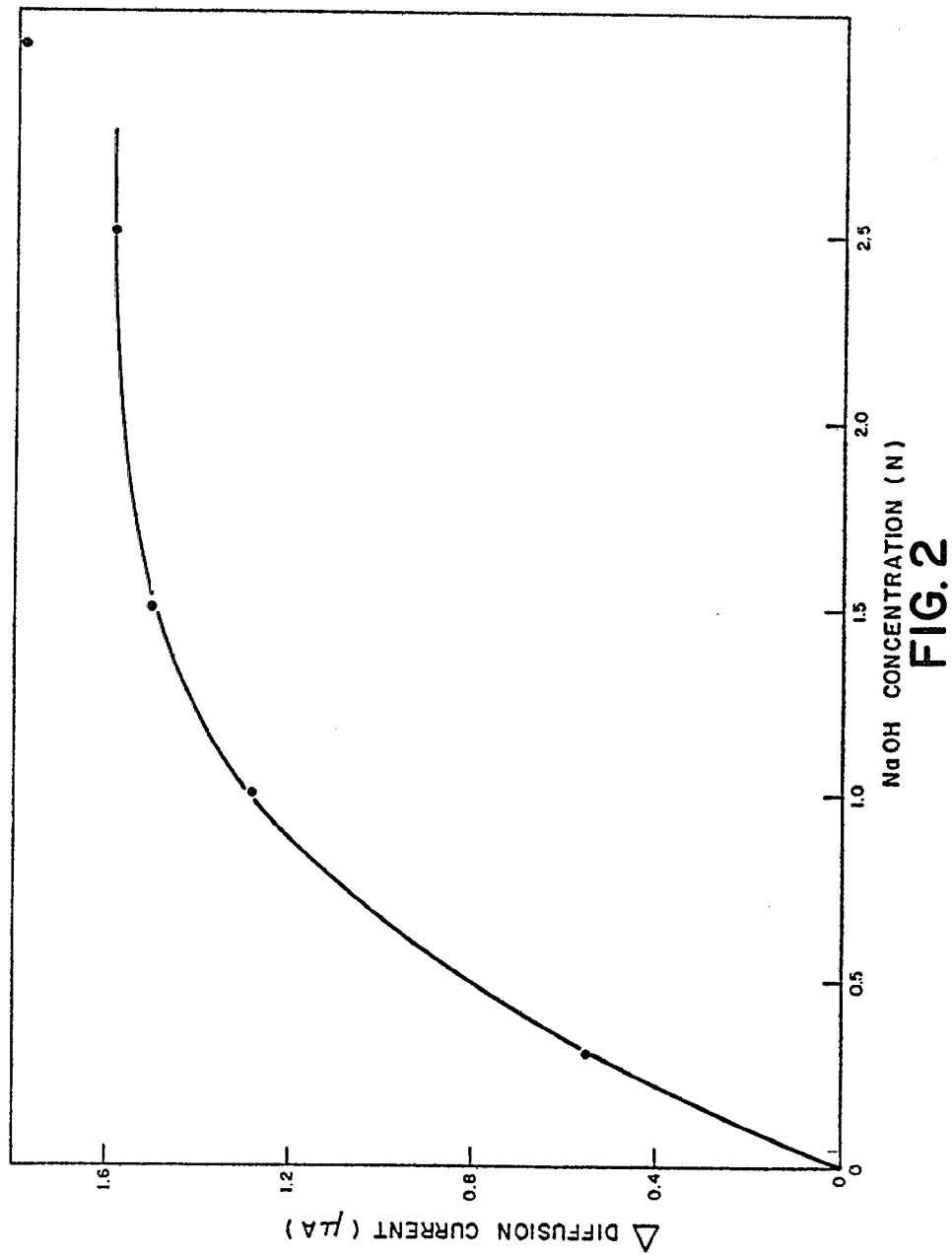
FIG. 2 is a plot of the difference in diffusion current of the effect of base concentration on the reactivity of glucose with 3,5-Dinitrosalicylic Acid, plotted versus the concentration of NaOH.

The Effect of Base Concentration on the Reactivity of Glucose with 3,5-Dinitrosalicylic Acid Five milliliters of a stock solution of 3,5-dinitrosalicylic acid, $8 \times 10^{-4}$ M 3,5-DNSA in 0.6 N NaOH, were transferred to a 10-ml volumetric flask. A volume of 0.1 ml of an aqueous $4 \times 10^{-2}$ M glucose standard was added and the solution was mixed. The flask was placed in a boiling water bath for five minutes, cooled, and brought to volume with distilled water. Polarographic analysis was performed as previously described. A blank test was similarly performed in the absence of glucose. The difference in the diffusion current ($\Delta I_d$) was calculated from the blank and test results (Table II). The above testing process was similarly performed for solutions containing NaOH at the following final molar concentrations: 1.0, 1.5, 2.0, 2.5, and 3.0. The $\Delta I_d$ results were plotted versus the concentration of NaOH (FIG. 2).

TABLE II

Effect of Base Concentration on the Diffusion Current of the 3,5-DNSA-Glucose Reaction

| Final NaOH Concentration (N) | Change in Diffusion Current ($\Delta I_d$ in $\mu$A) |
| --- | --- |
| 0.3 | 0.55 |
| 1.0 | 1.28 |
| 1.5 | 1.50 |
| 2.0 | 1.42 |
| 2.5 | 1.59 |
| 3.0 | 1.79 |

Reaction of Glucose with 3,5-Dinitrosalicylic acid in 0.25 N NaOH

Figure 3:
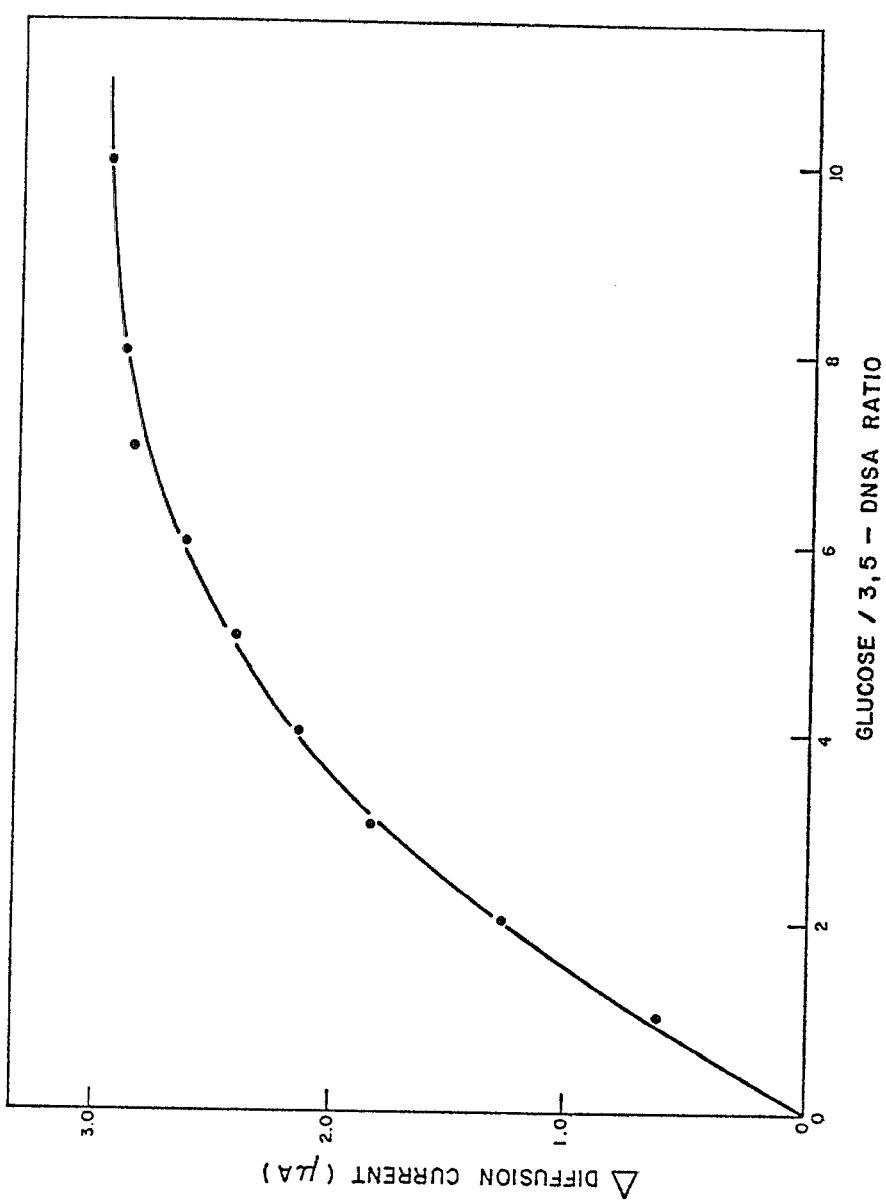
FIG. 3 is a plot of the difference in diffusion current of the reaction of glucose with 3,5-Dinitrosalicylic acid in 0.25 N NaOH, plotted versus the glucose: 3,5-DNSA molar ratio.

An $8.0 \times 10^{-4}$ M stock solution of 3,5-DNSA was prepared in aqueous 1.0 N NaOH. A stock solution of glucose was prepared by adding 3.6032 g to a 100-ml volumetric flask which was filled to volume with distilled water. Two and one-half milliliters of the 3,5-DNSA solution and 0.01 milliliters of the glucose solution were pipetted into a 10-ml volumetric flask and mixed. The flask was placed in a boiling water bath for 10 minutes, cooled, and filled to volume with distilled water. Polarographic analysis was performed as previously described. The above procedure was similarly performed with 3,5-DNSA blank solutions and also in the presence of larger volumes of glucose to evaluate glucose: 3,5-DNSA molar ratios ranging between 1:1 and 10:1. The $\Delta I_d$ was calculated for each test solution (Table III). The $\Delta I_d$ results were plotted versus the glucose: 3,5-DNSA molar ratio (FIG. 3).

TABLE III

Effect of Glucose Concentration on the Diffusion Current of the 3,5-DNSA Reduction Wave

| Glucose/3,5-DNSA Ratio | Change in Diffusion Current ($\Delta I_d$ in $\mu$A) |
| --- | --- |
| 0 | 0 |
| 1 | 0.62 |
| 2 | 1.27 |
| 3 | 1.84 |
| 4 | 2.15 |
| 5 | 2.42 |
| 6 | 2.64 |
| 7 | 2.87 |
| 8 | 2.91 |
| 10 | 2.98 |

Reaction of Glucose with 3,5-Dinitrosalicylic Acid in 3.0 N NaOH

Figure 4:
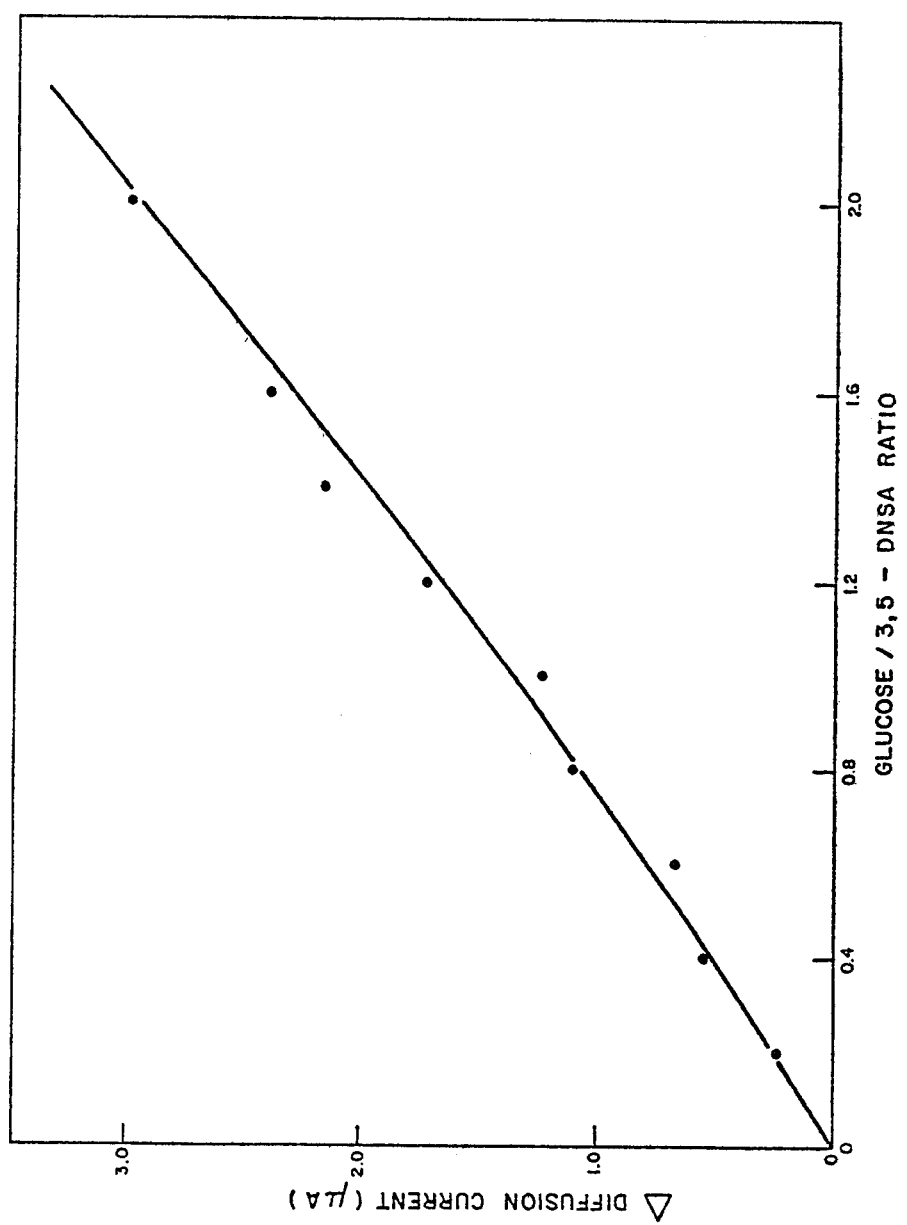
FIG. 4 is a plot of the difference in diffusion current of the reaction of glucose with 3,5-Dinitrosalicylic acid in 3.0 N NaOH, plotted versus the glucose: 3,5-DNSA molar ratio.

Five milliliters of a stock 3,5-dinitrosalicylic acid solution, $8 \times 10^{-4}$ M 3,5-DNSA in 0.6 N NaOH, and 4.5 ml of 6.0 N NaOH, were pipetted into a 10-ml volumetric flask. A volume of 0.01 milliliters of an aqueous $8 \times 10^{-2}$ M glucose standard was added and the flask was filled to the mark with distilled water. The solution was mixed and polarographic analysis was performed as previously described. Blank solutions and working standards were similarly prepared and analysed to evaluate glucose: 3,5-DNSA molar ratios between 0:1 and 2:1 in increments of 0.2. The $\Delta I_d$ results were calculated and plotted versus the glucose: 3,5-DNSA molar ratio (Table IV and FIG. 4).

TABLE IV

Effect of Glucose on the Diffusion Current of the 3,5-DNSA Reduction Wave

| Glucose/3,5-DNSA Ratio | Change in Diffusion Current ($\Delta I_d$ in $\mu A$) |
|---|---|
| 0 | 0 |
| 0.2 | 0.24 |
| 0.4 | 0.55 |
| 0.6 | 0.67 |
| 0.8 | 1.10 |
| 1.0 | 1.24 |
| 1.2 | 1.73 |
| 1.4 | 2.17 |
| 1.6 | 2.40 |
| 2.0 | 2.99 |

Figure 5:
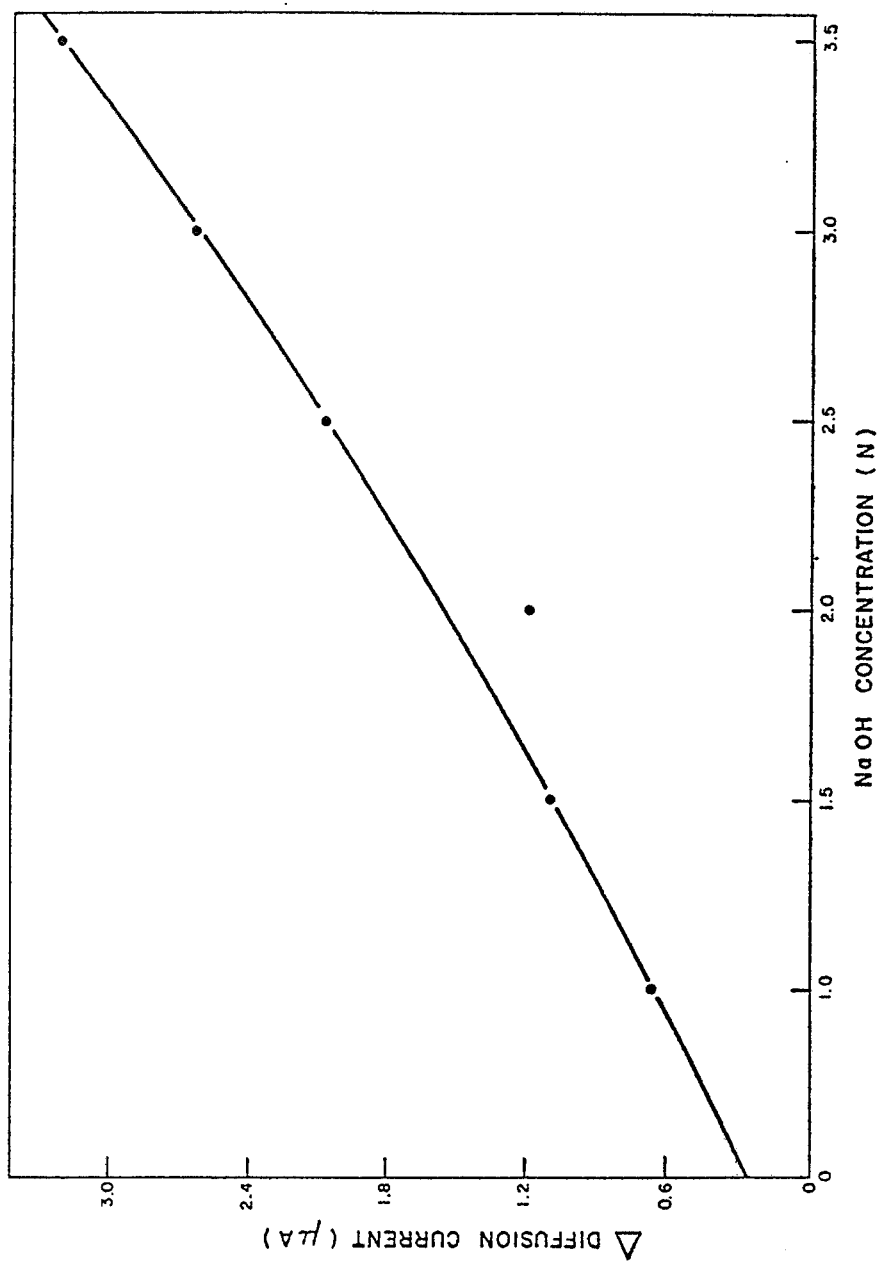
FIG. 5 is a plot of the difference in diffusion current of the effect of base concentration of the reactivity of glucose with 3,5-Dinitrobenzoic acid, plotted versus the concentration of NaOH.

The Effect of Base Concentration on the Reactivity of Glucose with 3,5-Dinitrobenzoic Acid A stock solution of 3,5-dinitrobenzoic acid was prepared by adding 17.0 mg of 3,5-DNBA and 16.7 milliliters of 6 N NaOH to a 100-ml volumetric flask which was filled to the mark with distilled water. A stock solution of glucose was prepared by adding 762.7 mg to a 50-ml volumetric flask which was filled to volume with distilled water. A test solution was prepared by adding 5 milliliters of the 3,5-DNBA solution, 0.1 milliliters of the glucose solution, and 0.83 milliliters of 6 N NaOH to a 10-ml volumetric flask which was filled to volume with distilled water. The final NaOH concentration was 1.0 N. The test solution was mixed and placed into a boiling water bath for 5 minutes. The solution was cooled to room temperature and polarographic analysis was performed as previously described. The above procedure was similarly performed for test solutions containing final NaOH concentrations of 1.5, 2.0, 2.5, 3.0, and 3.5 N. Blank solutions were similarly prepared and tested for each base concentration studied. The difference in diffusion current ($\Delta I_d$) was calculated for each of the corresponding blank and test results (Table V). The $\Delta I_d$ results were plotted versus the concentration of NaOH (FIG. 5).

TABLE V

Effect of Base Concentration on the Diffusion Current of the 3,5-DNBA-Glucose Reaction

| Final NaOH Concentration (N) | Change in Diffusion Current ($\Delta I_d$ in $\mu A$) |
|---|---|
| 1.0 | 0.67 |
| 1.5 | 1.10 |
| 2.0 | 1.20 |
| 2.5 | 2.08 |
| 3.0 | 2.64 |
| 3.5 | 3.21 |

Reaction of Glucose with 3,5-Dinitrobenzoic Acid in 0.75 N NaOH

Figure 6:
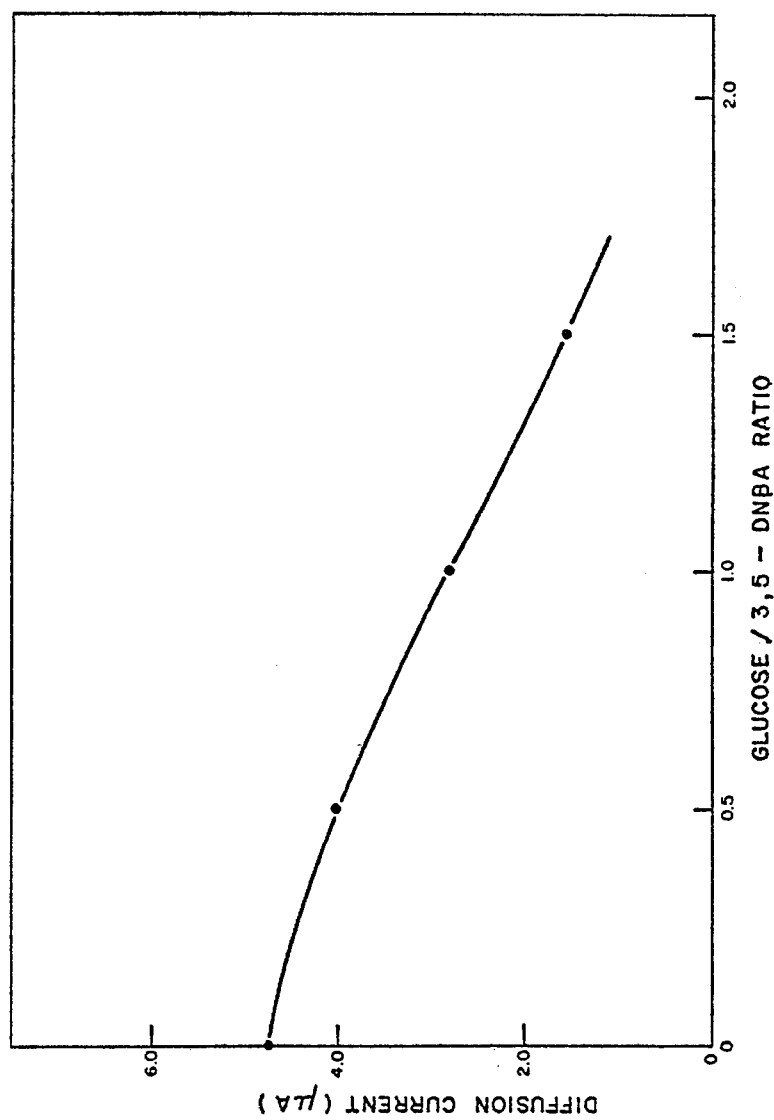
FIG. 6 is a plot of the difference in diffusion current of the reaction of glucose with 3,5-Dinitrobenzoic acid in 0.75 N NaOH, plotted versus the glucose: 3,5-DNBA molar ratio.

An $8.0 \times 10^{-4}$ M stock solution of 3,5-dinitrobenzoic acid was prepared in aqueous 1.0 N NaOH. A test solution was prepared by adding 5.0 milliliters of 3,5-DNBA solution, 10 $\mu l$ of a 0.2 M glucose solution, and 1.25 milliliters of 2.0 N NaOH to a 10-ml volumetric flask. The glucose: 3,5-DNBA molar ratio was 0.5:1. The solution was mixed, incubated in a boiling water bath for 5 minutes, cooled, and brought to volume with distilled water. Polarographic analysis was performed as previously described. A blank was similarly prepared and tested in the absence of glucose. The above procedure was similarly performed for glucose and 3,5-DNBA at molar ratios of 1:1 and 1.5:1. The diffusion current was calculated for each test solution and the results were plotted versus the Glucose: 3,5-DNBA molar ratio (Table Vi and FIG. 6).

TABLE VI

Effect of Glucose on the Diffusion Current of the 3,5-DNBA Reduction Waves

| Glucose/3,5-DNBA | Diffusion Current ($\mu A$) |
|---|---|
| 0 | 4.74 |
| 0.5 | 4.02 |
| 1.0 | 2.83 |
| 1.5 | 1.57 |

Analysis of Glucose in Biological Fluids

Glucose in Serum

Figure 7:
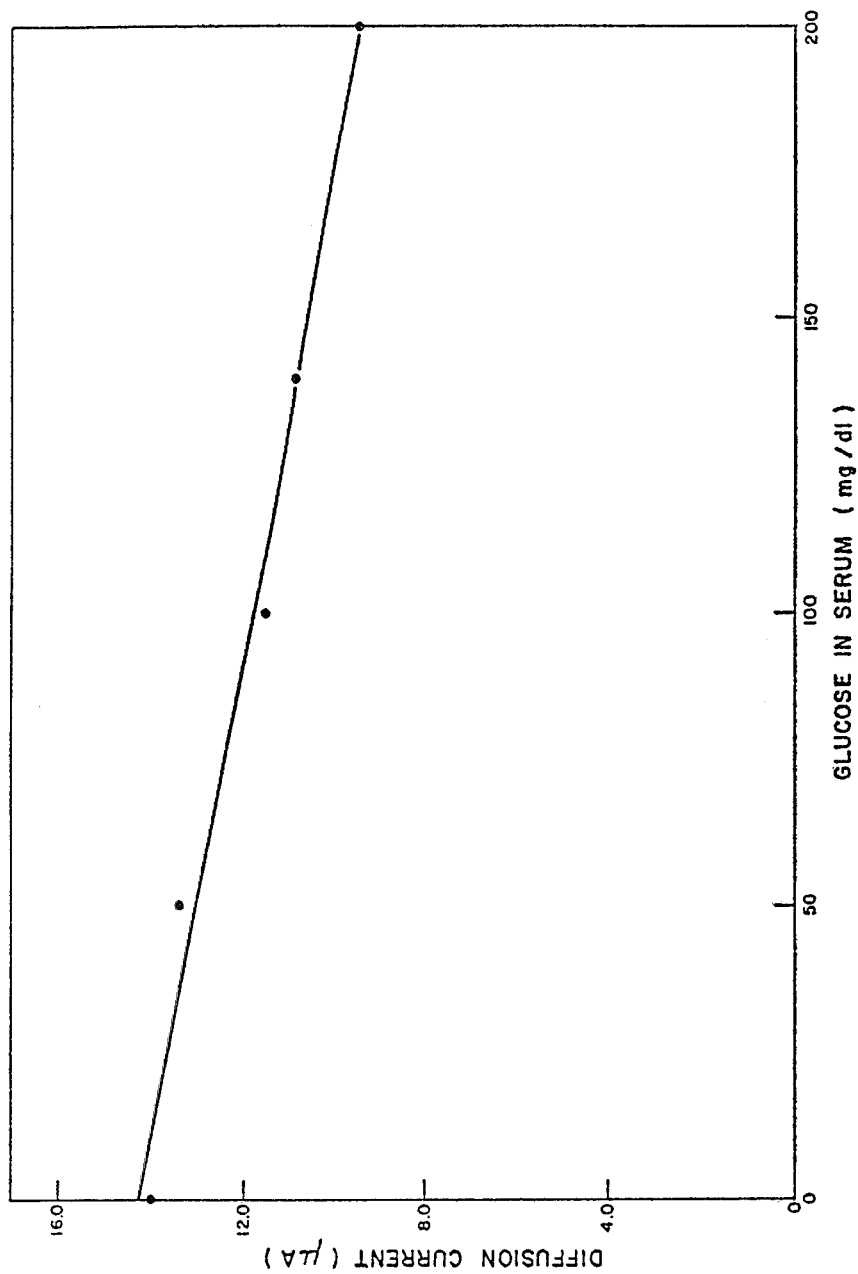
FIG. 7 is a plot of the total diffusion current for the nitro group reduction waves plotted versus the quantity of glucose added to glucose in serum.

A stock solution of 3,5-dinitrobenzoic acid was prepared by adding 8.5 mg of 3,5-DNBA and 10.0 milliliters of 6 N NaOH to a 100-ml volumetric flask which was filled to the mark with distilled water. One milliliter of "normal" serum was deproteinized by adding 1.0 milliliter of trichloroacetic acid, mixing the solution vigorously, and centrifuging. Five milliliters of 3,5-DNBA solution, 0.1 milliliters of deproteinized serum, and 4.5 milliliters of 6 N NaOH were added to a 10-ml volumetric flask. The flask was filled to the mark with distilled water, mixed, and placed in a boiling water bath for 5 minutes. The test solution was brought to room temperature and polarographic analysis was performed as previously described. The above procedure was similarly performed for four aliquots for serum containing standard additions of glucose at 50, 100, 140, and 200 mg/100 ml of serum. The total diffusion current for the nitro group reduction waves was recorded for each test solution (Table VII). The $I_d$ results were plotted versus the quantity of glucose added (FIG. 7).

TABLE VII

Effect of Deproteinized Serum and Glucose Standard Additions on the Diffusion Current of the 3,5-DNBA Composite Wave

| Glucose Addition (mg/100 ml) | Diffusion Current ($\mu A$) |
|---|---|
| 0 | 14.0 |
| 50 | 13.0 |
| 100 | 11.5 |
| 140 | 10.9 |
| 200 | 9.5 |

Glucose in Urine

Figure 8:
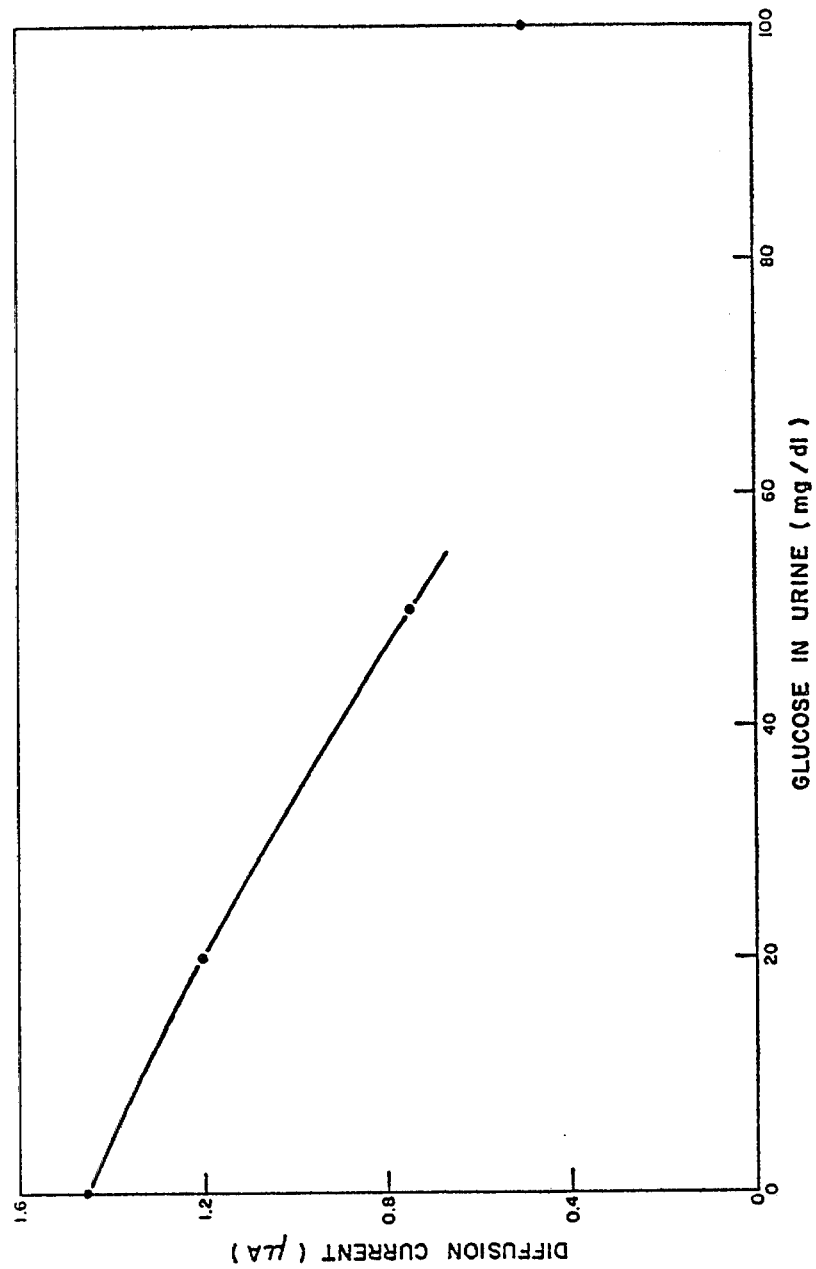
FIG. 8 is a plot of the total diffusion current for the nitro group reduction waves plotted versus the quantity of glucose added to glucose in urine.

A stock solution of 3,5-dinitrobenzoic acid was prepared by adding 8.5 mg of 3,5-DNBA and 10.0 milliliters of 6 N NaOH to a 100-ml volumetric flask which was filled to the mark with distilled water. Five milliliters of the 3,5-DNBA solution, 50 $\mu l$ of "normal" urine, and 4.5 milliliters of 6 N NaOH were added to a 10-ml volumetric flask. The flask was filled to the mark, mixed, and placed in a boiling water bath for.5 minutes. The test solution was brought to room temperature and polarographic analysis was performed as previously described. The above procedure was similarly performed for three aliquots of urine containing standard additions of glucose at 20, 50, and 100 mg/100 ml of urine. The total diffusion current for the nitro group reduction waves were recorded for each test solution (Table VIII). The $I_d$ results were plotted versus the quantity of glucose added (FIG. 8).

TABLE VIII

| Effect of Urine and Glucose Standard Additions on the Total Diffusion Current of the 3,5-DNBA Waves ||
|---|---|
| Glucose Addition (mg/100 ml) | Diffusion Current (μA) |
| 0 | 1.46 |
| 20 | 1.20 |
| 50 | 0.75 |
| 100 | 0.50 |

The addition of sodium chloride to the test solution has improved the overall appearance of the nitro reduction waves. Optimal improvement is noted for aromatic compounds containing two or three nitro groups. The usually difficult to measure second and third nitro reduction waves are well defined and can easily be measured.

REFERENCES

1. Meur, S. K., Rao, V. S., De, K. B., Spectrophotometric Estimation of Reducing Sugars by Variation of pH. Fresenius Z. Anal. Chem. 283, 195 (1977)
2. Gindler, E. M., Determination of Amylase. U.S. Pat. No. 3,953,297 (Apr. 1976).
3. Gindler, E. M., Determination of Amylase. U.S. Pat. No. 3,869,348 (Mar. 1975).
4. Van Bezeij, M., and Bosch, M. W., An Unequivocal Method for Blood Sugar Determination Using Dinitrosalicylic Acid as the Color Reagent. Pharm. Weekbl. 111,505 (1976)
5. Scholze, D., Rapid Method for the Analysis of Reducing Substances in Beet Pulp. Lebensm.-Ing. 21,255 (1974)
6. Bittman, R., Analysis of Reducing Sugars in Breakfast Cereal and Other Foods. J. of Chem. Educ. 51,46 (1974)
7. Amador, E., Automated Urinary Glucose Analyses. Am. J. Clin. Path. 59, 735 (1973)
8. Searcy, R. L., Hayashi, S., and Berk, J. E., A New Micro Saccharogenic Method for Serum Amylase Determination. Am. J. Clin. Path. 46, 582 (1966)
9. Fingerhut, B., Ferzola, R., Poock, A., and Marsh, W. H., A Rapid Saccharogenic Method for the Determination of Serum Amylase. Clin. Chem. 11, 862 (1965)
10. Henry, R. J., and Chiamori, N., Study of the Saccharogenic Method for the Determination of Serum and Urine Amylase. Clin. Chem. 5, 434 (1960)
11. Kozlov, V. V., and Khrustaleva, V. M., Colorimetric Method of Determination of Carbohydrates with Dinitrosalicylic Acid. Sbornik Nauch. Prabot. Moskov. Inst. Narod. Khoz. 10, 353 (1957)
12. Bell, D. J., Manners, D. J., and Palmer, A., Observations on the Reaction of Alkaline 3,5-Dinitrosalicylate by Certain Carbohydrates. J. Chem. Soc. London. 3760 (1952).
13. Hostettler, F., Borel, E., and Deuel, H., Über die Reduktion 3,5-Dinitrosalicylsäure durch Zucker. Helv. Chim. Acta. 34, 2132 (1951)
14. Brodersen, R., and Ricketts, T., Evaluation of a Modified Sumner's Method (Dinitrosalicylic Acid) for Determination of Glucose in Urine. J. Lab. Clin. Med. 34, 1447 (1949).
15. Leech, R. S., and Woodford, N., A Simple Bedside Method for the Estimation of Blood Sugar. J. Lab. & Clin. Med. 33, 644 (1948)
16. Sumner, J. B., and Sisler, E. B., A Simple Method for Blood Sugar. Arch. Biochem. 4, 333 (1944)
17. Short, J. J., Note on the Sumner Method for Sugar in Urine. J. Lab. & Clin. 18, 641 (1933)
18. Sumner, J. B., A More Specific Reagent for the Determination of Sugar in Urine. J. Biol. Chem. 65, 393 (1925)
19. Sumner, J. B., The Estimation of Sugar in Diabetic Urine, Using Dinitrosalicylic Acid. J. Biol. Chem. 62, 287 (1924).
20. Sumner, J. B., Dinitrosalicylic Acid: A Reagent for the Estimation of Sugar in Normal and Diabetic Urine. J. Biol. Chem. 47, 5 (1921)

What I claim is:

1. An electrochemical process to determine the concentration of glucose in serum samples, other fluids or solids brought into solution, whereby glucose is reacted with an aromatic reagent containing one or more nitro groups, and the chemical reaction is monitored at electrodes which measure the current produced by the reaction of one or more of the nitro groups.

* * * * *